United States Patent [19]

Crenshaw et al.

[11] 4,208,521
[45] Jun. 17, 1980

[54] PROCESS FOR THE PREPARATION OF IMIDAZO[2,1-b]QUINAZOLINONES

[75] Inventors: Ronnie R. Crenshaw, Dewitt; Thomas A. Montzka, Manlius, both of N.Y.

[73] Assignee: Bristol-Myers Company, New York, N.Y.

[21] Appl. No.: 929,627

[22] Filed: Jul. 31, 1978

[51] Int. Cl.$^2$ .................................... C07D 487/04
[52] U.S. Cl. .......................................... 544/250
[58] Field of Search ....................... 544/250; 424/251

[56] References Cited

U.S. PATENT DOCUMENTS

| | | | |
|---|---|---|---|
| 3,932,407 | 1/1976 | Beverung, Jr. et al. | 544/250 |
| 3,983,119 | 9/1976 | Beverung, Jr. et al. | 544/250 |
| 3,988,340 | 10/1976 | Partyka et al. | 544/250 |

OTHER PUBLICATIONS

Palmer, "The Structure and Reactions of Heterocyclic Compounds", Edward Arnold, (Publishers) Ltd., London, (1967), pp. 78–79.
Freeman et al., Aust. J. Chem., (1978), vol. 31, pp. 179–186.
Annual Review of Biochemistry, vol. 37, pp. 701–702, (1968).

*Primary Examiner*—Donald G. Daus
*Assistant Examiner*—Diana G. Rivers
*Attorney, Agent, or Firm*—Richard R. Lloyd

[57] ABSTRACT

Known cardiovascular agents of the formula

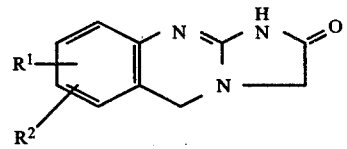

wherein $R^1$ and $R^2$ are each independently hydrogen, (lower)alkyl, (lower)alkoxy, (lower)alkylthio, trifluoromethyl, hydroxy, nitro, chloro, bromo or fluoro are prepared by reacting a compound of the formula

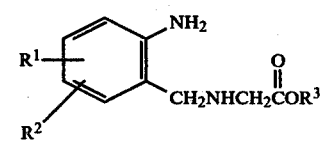

in which $R^1$ and $R^2$ are as described above and $R^3$ is hydrogen, (lower)alkyl or aryl, with a compound of the formula

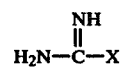

in which X is a leaving group as described herein.

10 Claims, No Drawings

PROCESS FOR THE PREPARATION OF IMIDAZO[2,1-b]QUINAZOLINONES

SUMMARY OF THE INVENTION

This application relates to a novel process for the preparation of known cardiovascular agents of Formula I, which comprises reacting an optionally substituted N-(2-aminobenzyl)glycine alkyl ester of Formula II with a substituted carboxamidine of Formula III.

DESCRIPTION OF THE PRIOR ART

U.S. Pat. No. 3,932,407 discloses compounds of the formula

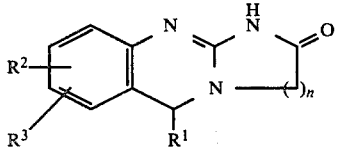

in which $R^1$ is H, phenyl or (lower)alkyl, $R^2$ and $R^3$ when alike are H, chloro, bromo, fluoro, (lower)alkyl, hydroxy or (lower)alkoxy, $R^2$ and $R^3$ when different are H, chloro, bromo, fluoro, $SO_3H$, $CF_3$, hydroxy, nitro, amino, phenyl, (lower)alkyl of 1 to 3 carbon atoms or (lower)alkoxy of 1 to 3 carbon atoms, or when taken together $R^2$ and $R^3$ are methylenedioxy or the residue of a phenyl ring, and n is an integer of 1 or 2; and pharmaceutically acceptable acid addition salts thereof. The compounds, which are disclosed as hypotensive, blood platelet antiaggregative and/or bronchodilator agents, are prepared inter alia by a multistep process ending in the reaction of CNBr with an ethanol solution of a compound of the formula

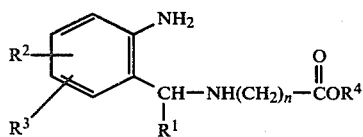

in which $R^1$, $R^2$, $R^3$ and n are as described above, and $R^4$ is (lower)alkyl. In an alternate procedure, some of the above compounds are prepared by the following reaction sequence, wherein $R^2$ is as described above:

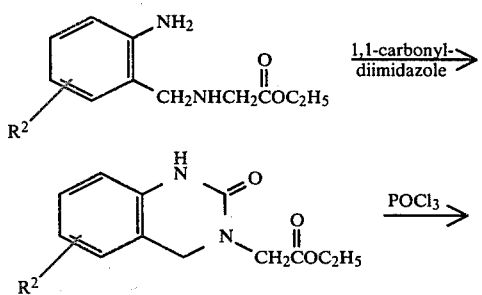

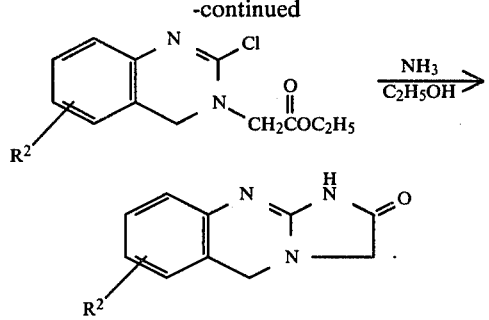

U.S. Pat. No. 3,983,119 discloses a process for the preparation of compounds of the formula

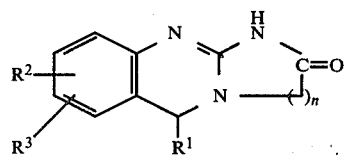

in which $R^1$ is (lower)alkyl of 1–6 carbon atoms and $R^2$ and $R^3$ are each independently hydrogen, chloro, bromo, fluoro, sulfonate, trifluoromethyl, (lower)alkyl, hydroxy, nitro, amino, (lower)alkoxy or phenyl, or when taken together $R^2$ and $R^3$ are methylenedioxy or the residue of a phenyl ring, and n is 1 or 2, by the following reaction scheme:

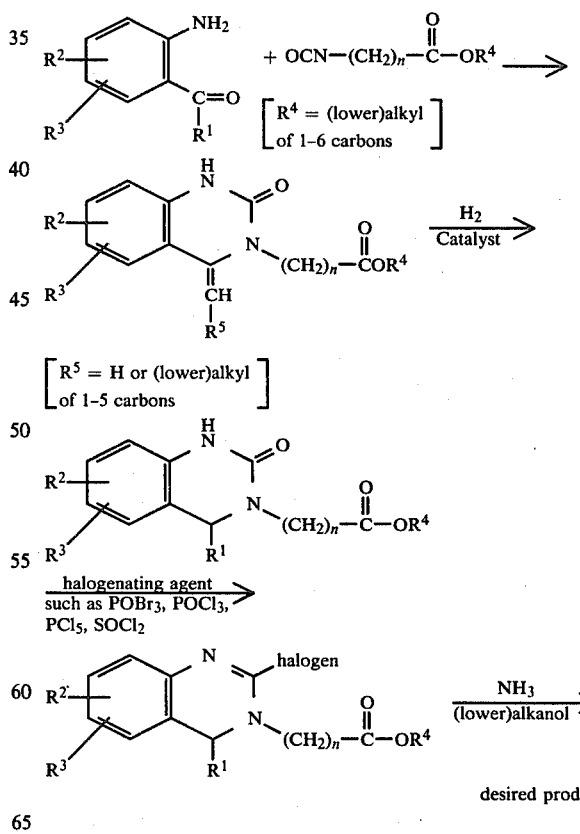

desired product

U.S. Pat. No. 3,983,120 discloses a process for the preparation of the same compounds as U.S. Pat. No. 3,983,119 by the following reaction scheme:

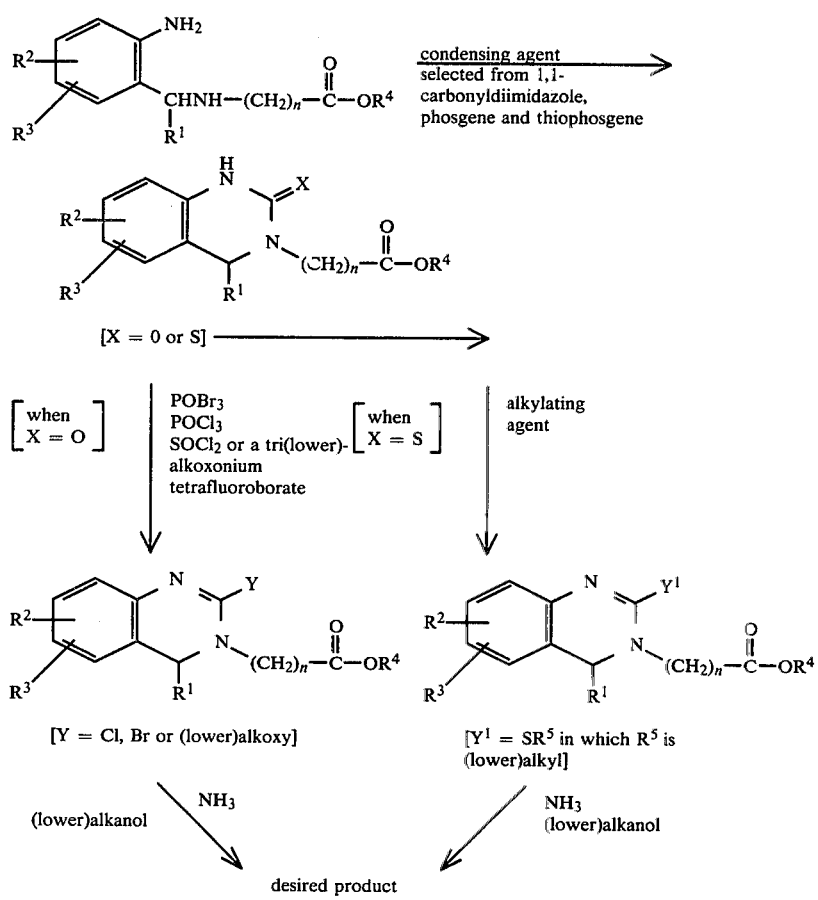

The use of substituted carboxamidines of Formula III for the preparation of guanidines is well known, as described, for example, in Annual Review of Biochemistry, 37, 701-2 (1968), which discusses the use of such reagents as S-methylisothiourea and 1-guanyl-3,5-dimethylpyrazole for guanidation of proteins.

COMPLETE DISCLOSURE

This application relates to cardiovascular agents. More particularly, this application relates to a process for the preparation of known cardiovascular agents of the formula

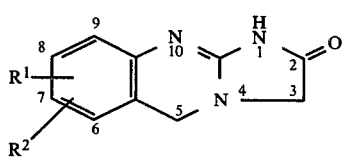

wherein $R^1$ and $R^2$ are each individually selected from hydrogen, (lower)alkyl, (lower)alkoxy, (lower)alkylthio, trifluoromethyl, hydroxy, nitro, chloro, bromo and fluoro, and nontoxic, pharmaceutically acceptable acid addition salts thereof, which process comprises reacting a compound of the formula

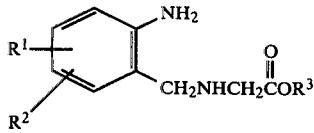

wherein $R^1$ and $R^2$ are as defined above, and $R^3$ is hydrogen, (lower)alkyl, phenyl or substituted phenyl, in an inert organic solvent, with about an equimolar amount of a compound of the formula

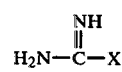

and preferably an acid addition salt thereof, wherein X is a leaving group selected from amino, $SR^4$ in which $R^4$ is (lower)alkyl, phenyl or substituted phenyl, and an optionally substituted nitrogen-containing heterocyclic ring which is attached via its 1-position to the carboxamidine moiety.

For the purpose of this disclosure, the compounds produced by the process of the present invention are represented as having Formula I. However, these compounds can exist in several tautomeric forms, e.g.:

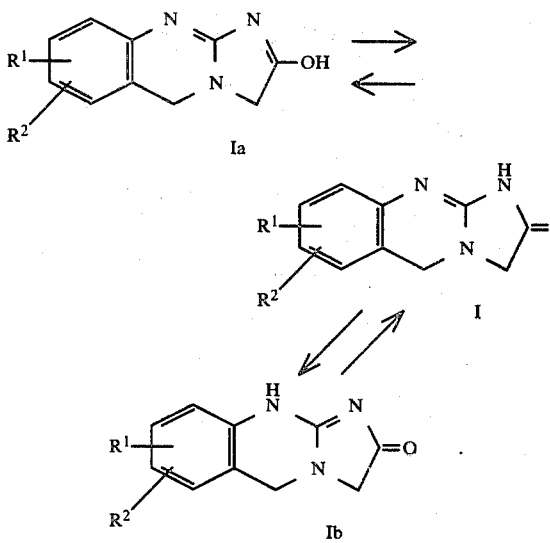

All possible tautomers are considered an integral part of the present invention and all such tautomers are considered included when the compounds are represented by Formula I.

Nontoxic pharmaceutically acceptable salts of the compounds of Formula I will be readily apparent to those skilled in the art. They include, for example, the hydrochlorides, hydrobromides, hydroiodides, (lower)alkylsulfates, (lower)alkylsulfonates, arylsulfonates, phosphates, sulfates, maleates, fumarates, succinates, tartrates, citrates and other acid addition salts commonly used in the art.

As used herein, the term "(lower)alkyl" means a straight or branched chain alkyl group containing from 1 to 6 carbon atoms. Similarly, the terms "(lower)alkoxy" and "(lower)-alkylthio" mean alkoxy and alkylthio groups, respectively, where the alkyl portion is straight or branched and contains from 1 to 6 carbon atoms.

The definitions of $R^3$ and $R^4$, above, each include "substituted phenyl". The term "substituted phenyl" is intended to include the phenyl group containing from 1 to 3 conventional substituent groups such as chloro, bromo, fluoro, iodo, (lower)alkyl, (lower)alkoxy, (lower)alkylthio, trifluoromethyl, nitro, and the like. Neither $R^3$ nor leaving group X (of which $R^4$ is a part) remain as substituents on the products of Formula I and the particular substituents on the phenyl ring are not critical except that they should be inert under the reaction conditions, i.e. should not enter into the reaction.

In one embodiment of the invention, leaving group X in the compound of Formula III may be an optionally substituted nitrogen-containing heterocyclic ring which is attached via its 1-position to the carboxamidine moiety. As discussed above, leaving group X does not remain as a substituent on the products of Formula I and the particular heterocyclic ring, or its substituents are not critical, provided only that they are inert under the reaction conditions. Typical heterocyclic rings which may be utilized include, for example, pyrrole, pyrazole, imidazole, triazole, tetrazole, indole, benzimidazole, and the like. Suitable substituent groups for the heterocyclic ring are as described above for phenyl substituents.

The reaction is conducted in a non-reactive organic solvent. Polar solvents are preferred but one may utilize any inert organic solvent in which the reactants have sufficient solubility. Preferred solvents include alkanols, dimethylacetamide, dimethylformamide, dimethylsulfoxide, acetonitrile, and the like. Lower alkanols are the most preferred solvents, e.g. ethanol, 1-propanol and 2-propanol.

The reaction may be conducted at a temperature up to about 200°. A preferred temperature range is from about 50° to about 150° and a more preferred range is from about 50° to about 100°.

In a preferred embodiment of the present invention, $R^1$ and $R^2$ are each independently selected from hydrogen, (lower)alkyl, (lower)alkoxy, chloro, bromo and fluoro. In a more preferred embodiment, $R^1$ and $R^2$ are each independently selected from hydrogen, (lower)alkyl, chloro, bromo and fluoro. In a still more preferred embodiment, $R^1$ and $R^2$ are each independently selected from hydrogen, methyl and chloro. In one most preferred embodiment, $R^1$ and $R^2$ are each chloro, and the resulting product of Formula I is 6,7-dichloro-1,5-dihydroimidazo[2,1-b]quinazolin-2(3H)-one. In another most preferred embodiment, $R^1$ is hydrogen and $R^2$ is methyl, and the resulting product of Formula I is 1,5-dihydro-6-methylimidazo[2,1-b]quinazolin-2(3H)-one.

In another aspect of this invention, $R^3$ preferably is (lower)alkyl and most preferably is ethyl. In still another aspect of the invention, leaving group X of the compound of Formula III preferably is selected from amino, $SR^4$ in which $R^4$ is (lower)alkyl [and most preferably methyl] and di(lower)-alkylpyrazol-l-yl [and most preferably 3,5-dimethylpyrazol-l-yl].

The starting materials of Formula II are prepared as described in U.S. Pat. Nos. 3,932,407 and 3,983,120, or by analogous procedures. The starting materials of Formula III are either known compounds or may be prepared by known procedures.

EXAMPLE 1

6,7-Dichloro-1,5-dihydroimidazo[2,1-b]quinazolin-2(3H)-one

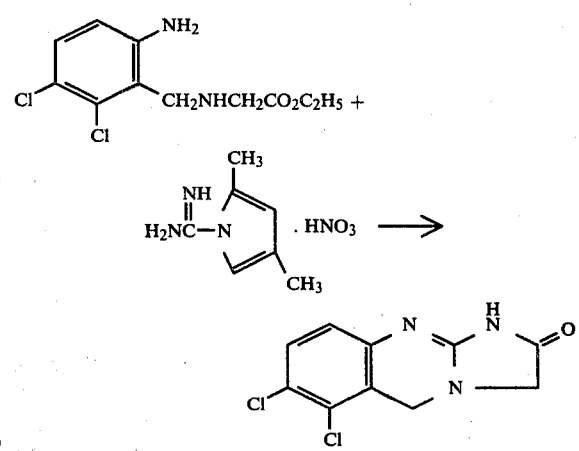

A mixture of N-(2-amino-5,6-dichlorobenzyl)glycine ethyl ester (2.77 g, 0.01 mole) and 3,5-dimethylpyrazole-1-carboxamidine nitrate (2.01 g, 0.01 mole) in absolute ethanol (30 ml) was heated at reflux for 24 hours. The mixture was filtered and the product was washed successively with ethanol, acetone and ether to yield the title compound (1.02 g, 40%); identical (ir, nmr) with authentic material prepared by a prior art procedure.

Anal. Calcd for $C_{10}H_7Cl_2N_3O$: C, 46.90; H, 2.76; N, 16.41. Found: C, 46.50; H, 2.76; N, 16.82.

EXAMPLE 2

1,5-Dihydro-6-methylimidazo[2,1-b]quinazolin-2(3H)-one

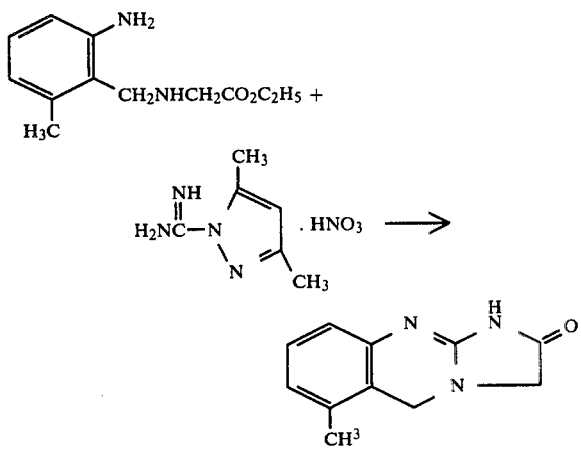

A mixture of N-(2-amino-6-methylbenzyl)glycine ethyl ester (1.097 g, 0.0049 mole) and 3,5-dimethylpyrazole-1-carboxamidine nitrate (0.993 g, 0.0049 mole) in absolute ethanol (15 ml) was heated at reflux for 64 hours. The mixture then was filtered and the product washed with hot ethanol to yield the title compound (0.610 g, 61%); identical (ir, nmr) with authentic material prepared according to the procedure of J. Med. Chem., 18, 224 (1975)).

EXAMPLE 3

1,5-Dihydro-6-methylimidazo[2,1-b]quinazolin-2(3H)-one

A mixture of N-(2-amino-6-methylbenzyl)glycine ethyl ester (0.58 g, 0.0026 mole) and quanidine carbonate (0.26 g, 0.0014 mole) in absolute ethanol was heated at reflux for 5 days. Workup as in Example 2 gave the title compound (0.126 g, 24%), identical (ir) with authentic material prepared according to the procedure of J. Med. Chem., 18, 224 (1975).

EXAMPLE 4

1,5-Dihydro-6-methylimidazo[2,1-b]quinazolin-2(3H)-one

A mixture of N-(2-amino-6-methylbenzyl)glycine ethyl ester (0.972 g, 0.00437 mole) and 2-methyl-2-thiopseudourea sulfate (0.609 g, 0.00219 mole) in absolute ethanol (15 ml) was stirred at reflux for 16 hours. Workup as in Example 2 gave the title compound (47 mg), identical (ir) with authentic material prepared according to the procedure of J. Med. Chem., 18, 224 (1975).

We claim:

1. A process for the preparation of a compound of the formula

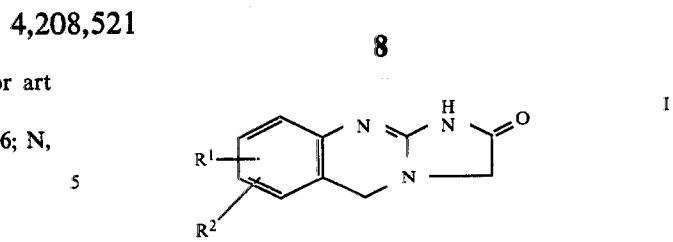

wherein $R^1$ and $R^2$ are each individually selected from hydrogen, (lower)alkyl, (lower)alkoxy, (lower)alkylthio, trifluoromethyl, hydroxy, nitro, chloro, bromo and fluoro, and nontoxic, pharmaceutically acceptable acid addition salts thereof, which process comprises reacting a compound of the formula

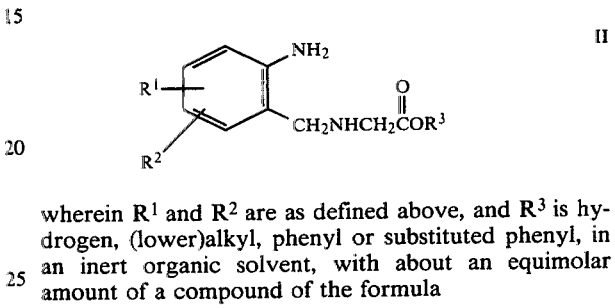

wherein $R^1$ and $R^2$ are as defined above, and $R^3$ is hydrogen, (lower)alkyl, phenyl or substituted phenyl, in an inert organic solvent, with about an equimolar amount of a compound of the formula

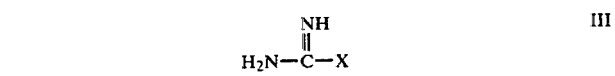

or an acid addition salt thereof, wherein X is a leaving group selected from amino, $SR^4$ in which $R^4$ is (lower)alkyl, phenyl or substituted phenyl, and a heterocyclic ring or substituted heterocyclic ring selected from pyrrole, pyrazole, imidazole, triazole, tetrazole, indole and benzimidazole, which is attached via its 1-position to the carboxamidine moiety.

2. The process of claim 1 wherein $R^1$ and $R^2$ are each independently selected from hydrogen, (lower)alkyl, (lower)-alkoxy, chloro, bromo and fluoro.

3. The process of claim 1 wherein $R^1$ and $R^2$ are each independently selected from hydrogen, (lower)alkyl, chloro, bromo and fluoro.

4. The process of claim 3 wherein $R^3$ is (lower)alkyl.

5. The process of claim 4 wherein leaving group X is a di(lower)alkylpyrazol-1-yl group.

6. A process for the preparation of 6,7-dichloro-1,5-dihydroimidazo[2,1-b]quinazolin-2(3H)-one which comprises reacting N-(2-amino-5,6-dichlorobenzyl)glycine ethyl ester with about an equimolar amount of an acid addition salt of 3,5-dimethylpyrazole-1-carboxamidine, in a (lower)alkanol solvent at a temperature above room temperature.

7. The process of claim 6 wherein the reaction is conducted in ethanol at reflux temperature.

8. A process for the preparation of 1,5-dihydro-6-methylimidazo[2,1-b]quinazolin-2(3H)-one which comprises reacting N-(2-amino-6-methylbenzyl)glycine ethyl ester with about an equimolar amount of an acid addition salt of 3,5-dimethylpyrazole-1-carboxamidine, in a (lower)alkanol solvent at a temperature above room temperature.

9. The process of claim 8 wherein the reaction is conducted in ethanol at reflux temperature.

10. A process of claim 7 or 9 wherein the 3,5-dimethylpyrazole-1-carboxamidine is in the form of its nitrate salt.

* * * * *

UNITED STATES PATENT AND TRADEMARK OFFICE
CERTIFICATE OF CORRECTION

PATENT NO. : 4,208,521

DATED : June 17, 1980

INVENTOR(S) : Ronnie R. Crenshaw and Thomas A. Montzka

It is certified that error appears in the above–identified patent and that said Letters Patent are hereby corrected as shown below:

In Example 1, the structural formula in Column 6, Lines 50-55, should be

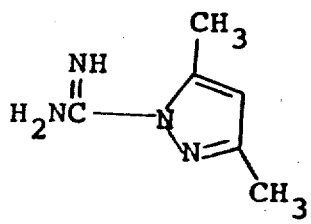

In Column 8, Line 40, "(lower)-alkoxy" should read -- (lower)alkoxy --.

Signed and Sealed this

Twenty-sixth Day of August 1980

[SEAL]

Attest:

SIDNEY A. DIAMOND

Attesting Officer        Commissioner of Patents and Trademarks